US012313546B2

(12) United States Patent
Kornbluth et al.

(10) Patent No.: US 12,313,546 B2
(45) Date of Patent: *May 27, 2025

(54) SENSING DEVICES AND CHEMOSENSORS AND COMPOSITIONS RELATING THERETO

(71) Applicant: Robert Bosch GmbH, Stuttgart (DE)

(72) Inventors: Mordechai Kornbluth, Brighton, MA (US); Kaushal Sagar, Singapore (SG)

(73) Assignee: Robert Bosch GmbH, Stuttgart (DE)

( * ) Notice: Subject to any disclaimer, the term of this patent is extended or adjusted under 35 U.S.C. 154(b) by 413 days.

This patent is subject to a terminal disclaimer.

(21) Appl. No.: 16/942,232

(22) Filed: Jul. 29, 2020

(65) Prior Publication Data

US 2022/0034808 A1   Feb. 3, 2022

(51) Int. Cl.
  *G01N 21/64* (2006.01)
  *C09K 11/07* (2006.01)
  *G01N 33/18* (2006.01)

(52) U.S. Cl.
  CPC .......... *G01N 21/643* (2013.01); *C09K 11/07* (2013.01); *G01N 33/1813* (2013.01); *C09K 2211/1037* (2013.01)

(58) Field of Classification Search
  CPC ..................... G01N 21/643; G01N 33/1813
  See application file for complete search history.

(56) References Cited

U.S. PATENT DOCUMENTS

| 11,193,891 | B2 * | 12/2021 | Kornbluth | G01N 33/84 |
| 2012/0156793 | A1 | 6/2012 | Higgs | |
| 2020/0158735 | A1 * | 5/2020 | Fahrni | G01N 21/6428 |

FOREIGN PATENT DOCUMENTS

| CN | 103641825 A | * | 3/2014 | ............ A01N 43/78 |
| CN | 107629044 A | * | 1/2018 | |
| CN | 108864046 A | * | 11/2018 | ........... C07D 401/12 |
| DE | 102020216352 A1 | | 6/2021 | |
| KR | 1020140081259 A | | 7/2014 | |
| WO | WO-2021121613 A1 | * | 6/2021 | ............. G01N 31/22 |

OTHER PUBLICATIONS

SciFinder CAS substance detail for CAS Registry No. 1023818-77-0; downloaded on Dec. 17, 2023. (Year: 2023).*
Khosrowabadi Kotyk, J.F. et al. "Copper tetradentate N2Py2 complexes with pendant bases in the secondary coordination sphere: improved ligand synthesis and protonation studies," Journal of Coordination Chemistry vol. 69, 2015, 1990-2002 (Year: 2015).*

(Continued)

*Primary Examiner* — Jennifer Wecker
*Assistant Examiner* — Michelle Adams
(74) *Attorney, Agent, or Firm* — BROOKS KUSHMAN P.C.

(57) ABSTRACT

A composition includes a 1,8-naphthalimide fluorophore, a spacer bound to the 1,8-naphthalimide fluorophore and a thiazole-based receptor having an unsaturated heterocycle ring bound to the spacer. The composition may be employed as a chemosensor configured to capture an ion in a fluid medium. The chemosensor may further be incorporated into a sensing device configured to detect the ion and calculate a concentration of the ion in the fluid medium.

16 Claims, 10 Drawing Sheets

(56) References Cited

OTHER PUBLICATIONS

Patil et al., "Overview of the chemosensor ligands used for selective detection of anions and metal ions ($Zn^{2+}$, $Cu^{2+}$, $Ni^{2+}$, $Co^{2+}$, $Fe^{2+}$, $Hg^{2+}$)", Inorganica Chimica Acta, May 24, 2018, https://doi.org/10.1016/j.ica.2018.05.026, 14 pages.

Petrenko et al., "Analysis and prediction of absorption band shapes, fluorescence band shapes, resonance Raman Intensities, and excitation profiles using the time-dependent theory of electronic spectroscopy", J. Chem. Phys. 127, 164319 (2007); https://doi.org/10.1063/1.2770706, 16 pages.

He et al., "A Fluorescent Chemosensor for Sodium Based on Photoinduced Electron Transfer", Anal. Chem. 2003, 75, 649-555, 7 pages.

Carter et al., "Fluorescent Sensors for Measuring Metal Ions in Living Systems", dx.doi.org/10.1021/cr400546e | Chem. Rev. 2014, 114, 4564-4601, 38 pages.

German Office Action, dated Feb. 28, 2023, received in related DE Application No. 10 2021 208 065.0. (Machine Translation provided).

Meiling Gao et al., "A new optical sensor for $Al^{3+}/Fe^{3+}$ based on PET and chelation-enhanced fluorescence," Res Chem. Intermed (2015) 41:9673-9685.

\* cited by examiner

SENSING DEVICES AND CHEMOSENSORS AND COMPOSITIONS RELATING THERETO

TECHNICAL FIELD

The present disclosure relates to compositions for ion sensing, for example, chemosensors employing the compositions and configured to sense ions in a fluid medium.

BACKGROUND

Securing the quality of drinking water has been a worldwide focus. Efforts have been made to remove contaminants in drinking water. Some of these contaminants are heavy metal ions, such as lead ions ($Pb^{2+}$), arsenic ions ($As^{3+}$ or $As^{5+}$), mercury ions ($Hg^{2+}$), chromium ions ($Cr^{2+}$), or cadmium ions ($Cd^{2+}$), which can pose detrimental health effects on humans. For example, $Pb^{2+}$ ions can enter cells and bind to proteins, inducing toxicity to the cells. Therefore, monitoring the levels of heavy metal ions in drinking water is of great importance.

SUMMARY

According to one embodiment, a composition for ion sensing is disclosed. The composition may include a fluorophore, a spacer bound to the fluorophore, and a receptor having an unsaturated heterocycle ring bound to the spacer. The spacer may be methylamine. The receptor and/or the spacer may have a receptor sidechain bound to the unsaturated heterocycle ring and/or a spacer sidechain bound to the methylamine, respectively. The receptor may include at least two electronegative atoms. The unsaturated heterocycle ring may be thiazole. The receptor sidechain may be a piperidinyl group or a sulfur-containing group. The spacer sidechain may be an alkyl group or a phenyl group. The fluorophore may be anthracene, benzene, carbazole, diphenylfurane, naphthalene, 1,8 naphthalimide, porphyrin, or pyrene.

According to another embodiment, a chemosensor configured to capture an ion in a fluid medium is disclosed. The chemosensor may include a fluorophore, a spacer bound to the fluorophore, and a receptor having an unsaturated heterocycle ring bound to the spacer. The spacer may be methylamine. The receptor and/or the spacer may have a receptor sidechain bound to the unsaturated heterocycle ring and/or a spacer sidechain bound to the methylamine, respectively. The receptor may include at least two electronegative atoms. The unsaturated heterocycle ring may be thiazole. The receptor sidechain may be a piperidinyl group or a sulfur-containing group. The spacer sidechain may be an alkyl group or a phenyl group. The fluorophore may be anthracene, benzene, carbazole, diphenylfurane, naphthalene, 1,8 naphthalimide, porphyrin, or pyrene.

According to yet another embodiment, a sensing device is disclosed. The sensing device may include a chemosensor configured to capture an ion and to generate a signal in response to capturing the ion, and a detector configured to collect the signal and to calculate a concentration of the ion in the fluid medium. The chemosensor may further include a fluorophore, a spacer bound to the fluorophore, and a receptor having an unsaturated heterocycle ring bound to the spacer. The spacer may be methylamine. The receptor and the spacer are configured to capture the ion to generate the signal. The receptor and/or the spacer may have a receptor sidechain bound to the unsaturated heterocycle ring and/or a spacer sidechain bound to the methylamine, respectively. The receptor may include at least two electronegative atoms. The unsaturated heterocycle ring may be thiazole. The receptor sidechain may be a piperidinyl group or a sulfur-containing group. The spacer sidechain may be an alkyl group or a phenyl group. The fluorophore may be anthracene, benzene, carbazole, diphenylfurane, naphthalene, 1,8 naphthalimide, porphyrin, or pyrene.

DETAILED DESCRIPTION

Figure 1:
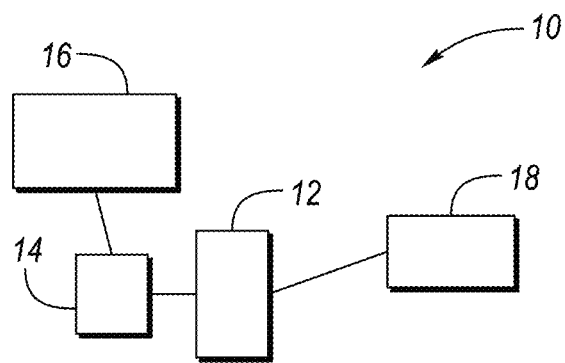
FIG. 1 depicts a schematic diagram of a chemosensor configured to detect ions in a fluid medium.

Embodiments of the present disclosure are described herein. It is to be understood, however, that the disclosed embodiments are merely examples and other embodiments can take various and alternative forms. The figures are not necessarily to scale; some features could be exaggerated or minimized to show details of components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for applications or implementations.

This present disclosure is not limited to the specific embodiments and methods described below, as specific components and/or conditions may, of course, vary. Furthermore, the terminology used herein is used only for the purpose of describing embodiments of the present disclosure and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The description of a group or class of materials as suitable for a given purpose in connection with one or more embodiments implies that mixtures of any two or more of the members of the group or class are suitable. Description of constituents in chemical terms refers to the constituents at the time of addition to any combination specified in the description and does not necessarily preclude chemical interactions among constituents of the mixture once mixed.

Except where expressly indicated, all numerical quantities in this description indicating dimensions or material properties are to be understood as modified by the word "about" in describing the broadest scope of the present disclosure.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

The term "substantially" may be used herein to describe disclosed or claimed embodiments. The term "substantially" may modify any value or relative characteristic disclosed or claimed in the present disclosure. "Substantially" may signify that the value or relative characteristic it modifies is within ±0%, 0.1%, 0.5%, 1%, 2%, 3%, 4%, 5% or 10% of the value or relative characteristic.

Reference is being made in detail to compositions, embodiments, and methods of embodiments known to the inventors. However, disclosed embodiments are merely exemplary of the present disclosure which may be embodied in various and alternative forms. Therefore, specific details disclosed herein are not to be interpreted as limiting, rather merely as representative bases for teaching one skilled in the art to variously employ the present disclosure.

Ion sensing techniques have been employed in detecting ions in a fluid medium (e.g. water). For example, fluorescence-based detection methods have been utilized to sense ions, including heavy metal ions, in water, where an ion binds to a detecting molecule (e.g. a chemosensor) to either generate or quench fluorescence. Measuring the fluorescence can subsequently determine an amount of the ion in the water.

However, because different ions have different sizes and require different binding energies when binding to different detecting molecules, the conventional fluorescence-based detection methods may exhibit different sensitivities toward the sensing of different ions. Therefore, to accurately detect the presence of a target ion in a fluid medium, a detecting molecule needs to selectively bind to the target ion with a high sensitivity.

Aspects of the present disclosure relate to a composition and a chemosensor employing the composition and configured to detect ions, especially $Pb^{2+}$ ions, in a fluid medium (e.g. water). In one embodiment, the chemosensor is a receptor-spacer-fluorophore type of sensor, where the spacer is methylamine, and the receptor includes an unsaturated heterocycle ring bound to the spacer and further includes at least one sidechain bound to the unsaturated heterocycle ring. In another embodiment, the chemosensor is a receptor-spacer-fluorophore type of sensor, where the spacer is methylamine with at least one sidechain, and the receptor includes an unsaturated heterocycle ring bound to the spacer. In yet another embodiment, the present disclosure relates to a sensing device incorporating a chemosensor and configured to determine an amount of an ion (e.g. $Pb^{2+}$ ion) in the fluid medium.

FIG. 1 depicts a schematic diagram of a chemosensor configured to detect ions (e.g. $Pb^{2+}$ ions) in a fluid medium (e.g. water). As shown in FIG. 1, the chemosensor 10 is a receptor-spacer-fluorophore type of sensor. Specifically, the chemosensor 10 includes a fluorophore 12. Non-limiting examples of the fluorophore 12 may be anthracene, benzene, carbazole, diphenylfurane, naphthalene, 1,8-naphthalimide, N,N,N',N'-tetramethylbenzidine, porphyrin, or pyrene.

The chemosensor 10 also includes a spacer 14 bound to the fluorophore 12. The spacer 14 may be methylamine, which may optionally include at least one sidechain attached thereto. Non-limiting examples of the at least one sidechain may be an alkyl group, a phenyl group, or an amine group.

Further, the chemosensor 10 includes a receptor 16 bound to the spacer 14 and configured to capture an ion (e.g. a $Pb^{2+}$ ion) in the fluid medium. The receptor 16 may include an unsaturated heterocycle ring bound to the spacer 14. The receptor 16 may also include at least one sidechain bound to the unsaturated heterocycle ring. The unsaturated heterocycle ring may be, but not limited to, thiazole, diazine, or pyridine. In some embodiments, the receptor 16 may include at least one electronegative atom, which may be, but not limited to, oxygen (O), nitrogen (N), or sulfur (S).

The chemosensor 10 may also include an anchor 18, which may link the chemosensor 10 to cellulose microparticles to immobilize the chemosensor 10. The anchor 18 may be diethyl sulfone. The cellulose microparticles may have a size in a range of 1 and 100 μm and may be embedded with hydrogels. The hydrogels may be, but not limited to, polyurethane or poly(2-hydroxyethyl methacrylate) (Poly-HEMA). In addition, the cellulose microparticles and the hydrogels may be supported by a polymer support, which may be, but not limited to, polyethylene terephthalate (PET).

Figure 2:
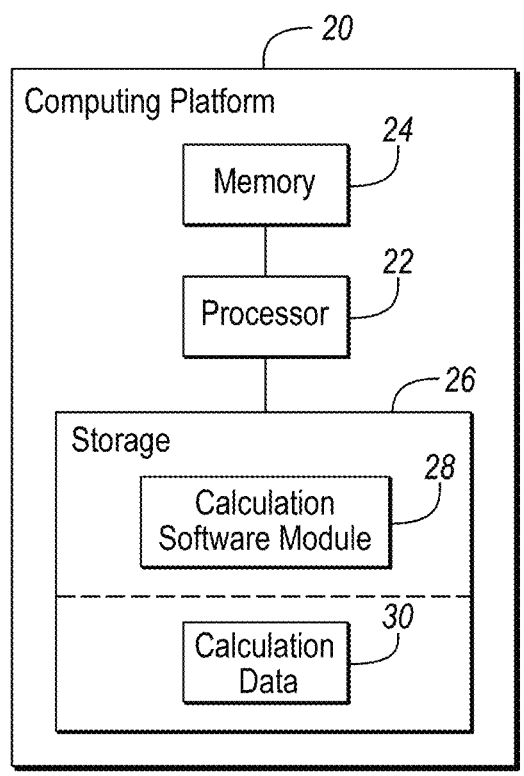
FIG. 2 depicts a schematic diagram of a computing platform that may be utilized to implement a quantum chemistry code, such as ORCA.

FIG. 2 depicts a schematic diagram of a computing platform that may be utilized to implement a quantum chemistry code, such as ORCA. The computing platform 20 may include a processor 22, a memory 24, and a non-volatile storage 26. The processor 22 may include one or more devices selected from high-performance computing (HPC) systems including high-performance cores, microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on computer-executable instructions residing in memory. The memory 24 may include a single memory device or a number of memory devices including random access memory (RAM), volatile memory, non-volatile memory, static random-access memory (SRAM), dynamic random-access memory (DRAM), flash memory, cache memory, or any other device capable of storing information. The non-volatile storage 26 may include one or more persistent data storage devices such as a hard drive, optical drive, tape drive, non-volatile solid-state device, cloud storage or any other device capable of persistently storing information.

The processor 22 may be configured to read into memory and execute computer-executable instructions residing in a calculation software module 28 of the non-volatile storage 26 and embodying algorithms, calculations and/or methodologies of one or more embodiments. The calculation software module 28 may include operating systems and applications. The calculation software module 28 may be compiled or interpreted from computer programs created using a variety of programming languages and/or technologies, including, without limitation, and either alone or in combination, Java, C, C++, C#, Objective C, Fortran, Pascal, Java Script, Python, Perl, and PL/SQL.

Upon execution by the processor 22, the computer-executable instructions of the calculation software module 28 may cause the computing platform 20 to implement one or more of the calculation algorithms and/or methodologies disclosed herein. The non-volatile storage 26 may also include calculation data 30 supporting the functions, features, calculations, and processes of the one or more embodiments described herein.

The program code embodying the algorithms and/or methodologies described herein is capable of being individually or collectively distributed as a program product in a variety of different forms. The program code may be distributed using a computer readable storage medium having computer readable program instructions thereon for causing a processor to carry out aspects of one or more embodiments. The computer readable storage medium, which is inherently non-transitory, may include volatile and non-volatile, and removable and non-removable tangible media implemented in any method or technology for storage of information, such as computer-readable instructions, data structures, program modules, or other data. The computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Computer readable program instructions may be downloaded to a computer, another type of programmable data processing apparatus, or another device from a computer readable storage medium or to an external computer or external storage device via a network.

Computer readable program instructions stored in the computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts or diagrams. In certain alternative embodiments, the functions, acts, and/or operations specified in the flowcharts and diagrams may be re-ordered, processed serially, and/or processed concurrently consistent with one or more embodiments. Moreover, any of the flowcharts and/or diagrams may include more or fewer nodes or blocks than those illustrated consistent with one or more embodiments.

Referring to FIG. 2, the computing platform 20 may be utilized to screen chemosensors that selectively bind to $Pb^{2+}$ ions with a high sensitivity. The computing platform 20 may compute energies and/or spectra for a given molecule. Specifically, the computing platform 20 may optimize a geometry of the given molecule using local-density approximation (LDA) or B3LYP hybrid functional with a conductor-like polarizable continuum solvation model (CPCM) and a Karlsruhe basis set def2-svp. The computing platform 20 may compute energies at possible binding sites and select a binding site that has the lowest binding energy. Further, the computing platform 20 may compute a total energy of the given molecule using second-order Moeller-Plesset perturbation theory with the resolution of the identity approximation (RI-MP2) as well as the solvation model CPCM and the basis set def2-svp. A basis set correction may be added under LDA up to def2-qzvpp. An independent correlation correction may further be added under def2-svp from domain-based local pair-natural orbital coupled cluster (DLPNO-CCSD(T)) approximations. Moreover, the computing platform 20 may compute fluorescence using an ORCA ASA or ORCA ESD module. The computing platform 20 may also compute charges using RI-MP2 with the solvation model CPCM and the basis set def2-svp based on a charge scheme such as Mulliken or Hirshfeld. In addition, a binding energy may be computed as an energy difference between an energy of an unbounded molecule plus an energy of an ion and an energy of a bounded molecule. Each ion may have an associated solvation energy not captured by the CPCM approximation, which may be neglected unless the ion is compared with each other.

Table 1 provides a group of molecules screened by the computing platform 20. Each molecule is composed of a thiazole-based receptor and a methylamine-based spacer. The thiazole-based receptor may further include at least one sidechain attached to the thiazole moiety thereof, and the spacer may also include at least one sidechain attached to the methylamine moiety thereof. Each molecule may bind to a fluorophore, 1,8-naphthalimide, to form a chemosensor. The fluorophore may further bind to an anchor, diethyl sulfone. Using the computing platform 20 described in FIG. 2, molecules that strongly bind to $Pb^{2+}$ ions can be determined.

Table 1 provides the binding energy (eV) between each molecule and a $Pb^{2+}$ ion. Table 1 also provides the MDL/MFCD/Chemspace identification (ID) (if available), the chemical abstracts service (CAS) number (if available), and the simplified molecular-input line-entry system (SMILES) of each molecule. Each molecule includes any stereoisomer it may be associated with.

| Molecule | Name | MDL/MFCD/Chemspace ID | CAS number | SMILES | $Pb^{2+}$ binding (eV) |
|---|---|---|---|---|---|
| 1 | 4-(1-aminoethyl)-N,N-dimethyl-1,3-thiazol-2-amine | MFCD20348605 | 1343806-45-0 | N[C@@H](c1csc(N(C)C)n1)C | −1.969 |

-continued

| Molecule | Name | MDL/MFCD/ Chemspace ID | CAS number | SMILES | $Pb^{2+}$ binding (eV) |
|---|---|---|---|---|---|
| 2 | 4-(Aminomethyl)-N,N-dimethyl-1,3-thiazol-2-amine | MFCD13857414 | 1023818-77-0 | NCc1csc(n1)N(C)C | −1.973 |
| 3 | N-[4-(Aminomethyl)-1,3-thiazol-2-yl-N-methylamine | MFCD19203221 | 1269400-66-9 | NCc1csc(NC)n1 | −1.754 |
| 4 | 4-(3-Aminopropyl)-1,3-thiazol-2-amine | MFCD08059800 | 136604-78-9 | Nc1nc(cs1)CCCN | −2.702 |
| 5 | 4-(3-Aminopropyl)-1,3-thiazol-2-amine | MFCD08059800 | 136604-78-9 | NCCCc1csc(n1)N | −2.062 |
| 6 | 2-Methyl-4,5,6,7-tetrahydro-1,3-benzothiazol-4-amine | MFCD09971182 | 70590-60-2 | N[C@H]1c2c(CCC1)sc(C)n2 | −1.834 |
| 7 | 1-{2-[(cyclohexylsulfanyl)methyl]-1,3-thiazol-4-yl}ethan-1-amine | MFCD21169714 | | N[C@@H](c1csc(CSC2CCCCC2)n1)C | −2.184 |
| 8 | 4-(1-aminoethyl)-N-[2-(dimethylamino)ethyl]-N-methyl-1,3-thiazol-2-amine | MFCD20348741 | | N[C@H](c1csc(n1)N(C)CCN(C)C)C | −2.415 |
| 9 | 4-(aminomethyl)-N-[3-(dimethylamino)methyl]-N-methyl-1,3-thiazol-2-amine | | | NCc1csc(n1)N(C)CN(C)C | −2.785 |
| a | 4-(2,4-dichlorophenyl)thiazol-2-amine | MFCD01114990 | 93209-97-3 | Nc1nc(cs1)c1ccc(cc1Cl)Cl | −1.446 |
| b | (5,6-Dihydroimidazo[2,1-b][1,3]thiazol-3-ylmethyl)amine | MFCD09702699 | 912771-25-6 | NCc1csc2n1CC[N]2 | −1.593 |
| c | 6,7-Dihydro-4H-pyrano[4,3-d]thiazol-2-amine | MFCD08690160 | 259810-12-3 | Nc1nc2c(COCC2)s1 | −1.256 |
| d | 4-[(3,5-dimethyl-1-piperidinyl)methyl]-1,3-thiazol-2-amine | MFCD08729213 | 929974-23-2 | Nc1nc(cs1)CN1C[C@@H](C[C@@H](C1)C)C | −2.471 |
| e | {2-[(3,5-dimethylpiperidin-1-yl)methyl]-1,3-thiazol-4-yl}methanamine | MFCD26698967 | | NCc1csc(CN2C[C@@H](C[C@@H](C2)C)C)n1 | −2.662 |
| f | 5-(3-fluorobenzyl)-1,3-thiazol-2-amine | MFCD05863658 | 884497-40-9 | Nc1ncc(Cc2ccc(ccc2)F)s1 | −0.734 |
| g | 1H-imidazol-4-ylmethanamine | MFCD01529873 | 13400-46-9 | NCc1c[nH]cn1 | −2.041 |
| h | (Imidazo[2,1-b][1,3]thiazol-6-ylmethyl)amine | MFCD06660668 | 449799-30-8 | NCc1cn2c(n1)scc2 | −1.981 |
| i | 1-(Imidazo[2,1-b]thiazol-6-yl)propan-1-amine | | 1255147-13-7 | N[C@@H](CC)c1cn2c(n1)scc2 | −1.97 |
| j | 1-(Imidazo[2,1-b]thiazol-6-yl)propan-2-amine | MFCD09889391 | 933698-28-3 | NC[C@@H](C)c1cn2c(n1)scc2 | −1.834 |
| k | 5-isobutyl-1,3-thiazol-2-amine | MFCD18816985 | 267658-06-0 | Nc1ncc(CC(C)C)s1 | −1.28 |
| m | 5-methoxy-1,3-thiazol-2-amine | MFCD01630757 | 59019-85-1 | Nc1ncc(OC)s1 | −1.311 |
| n | 5-methoxy-1,3-thiazol-2-methanamine | | | NCc1ncc(OC)s1 | −1.684 |
| o | 4-(2-methoxyphenyl)thiazol-2-amine | MFCD01535790 | 93209-95-1 | Nc1nc(cs1)c1ccccc1OC | −1.899 |
| p | (2-Methylthiazol-4-yl)methanamine | MFCD06212804 | 103694-26-4 | NCc1csc(C)n1 | −1.793 |
| q | 5-Methyl-4-(2-thienyl)-1,3-thiazol-2-amine | MFCD02734128 | 206555-52-4 | Nc1nc(c(C)s1)c1cccs1 | −1.457 |
| r | ({2-[(Methylthio)methyl]-1,3-thiazol-4-yl}methyl)amine | MFCD12198453 | 1210255-77-8 | NCc1csc(CSC)n1 | −2.241 |
| s | 4-(4-morpholinylmethyl)-1,3-thiazol-2-amine | MFCD06340096 | 3008-61-5 | Nc1nc(cs1)CN1CCOCC1 | −2.25 |

-continued

| Molecule | Name | MDL/MFCD/ Chemspace ID | CAS number | SMILES | $Pb^{2+}$ binding (eV) |
|---|---|---|---|---|---|
| t | 4-[(3-methyl-1-piperidinyl)methyl]-1,3-thiazol-2-amine | MFCD06655121 | 855715-26-3 | Nc1nc(cs1)CN1CC[C@@H](CC1)C | −2.525 |
| u | [2-(4-methylpiperidin-1-yl)-1,3-thiazol-4-yl]methanamine | MFCD20309730 | 1343840-41-4 | NCc1csc(n1)N1CC[C@@H](CC1)C | −1.898 |
| v | {2-[(4-methylpiperidin-1-yl)methyl]-1,3-thiazol-4-yl}methanamine | CSC016706396 | | NCc1csc(CN2CC[C@@H](CC2)C)n1 | −2.677 |
| w | 4-(1-piperidinyl)-1,3-thiazol-2-amine | MFCD11108800 | 1092289-19-4 | Nc1nc(cs1)N1CCCCC1 | −1.816 |
| x | 1-[2-(1-Piperidinyl)-1,3-thiazol-4-yl]methanamine | MFCD20309744 | 1083245-82-2 | NCc1csc(n1)N1CCCCC1 | −1.988 |
| y | (2-{[4-(propan-2-yl)piperidin-1-yl]methyl}-1,3-thiazol-4-yl)methanamine | CSC031393389 | | NCc1csc(CN2CC[C@@H](CC2)C(C)C)n1 | −2.691 |
| z | 1-[2-(2-Pyrimidinyl)-1,3-thiazol-4-yl]methanamine | MFCD12198485 | 1123169-55-0 | NCc1csc(c2ncccn2)n1 | −2.178 |
| A | 1-[2-(pyrrolidin-1-yl)-1,3-thiazol-4-yl]ethan-1-amine | MFCD20348573 | 1342194-70-0 | N[C@H](c1csc(n1)N1CCCC1)C | −1.958 |
| B | 1-(2-Pyrrolidin-1-yl-1,3-thiazol-4-yl)methanamine | MFCD13188551 | 1209952-47-5 | NCc1csc(n1)N1CCCC1 | −2.017 |
| C | 5,6-Dihydro-4H-pyrrolo[3,4-d]thiazole | MFCD18381179 | 721926-87-0 | N1Cc2c(C1)ncs2 | −0.687 |
| D | 1-{2-[(thian-2-yl)methyl]-1,3-thiazol-4-yl}ethan-1-amine | CSC048665216 | | N[C@@H](c1csc(C[C@H]2CCCCS2)n1)C | −2.268 |
| E | 1-thiazol-4-yl-ethylamine | MFCD06738792 | 885279-02-7 | N[C@@H](c1cscn1)C | −1.861 |
| F | 1-(1,3-thiazol-4-yl)propan-1-amine | MFCD23916952 | 1489019-51-3 | N[C@@H](c1cscn1)CC | −1.809 |
| G | 2-(1,3-Thiazol-4-yl)-2-propanamine | | 1501727-33-8 | NC(c1cscn1)(C)C | −1.832 |
| H | 1,3-Thiazol-4-amine | MFCD02094165 | 17720-99-9 | Nc1cscn1 | −1.333 |
| I | phenyl(1,3-thiazol-4-yl)methanamine | MFCD17276863 | 1480101-99-2 | N[C@@H](c1cscn1)c1ccccc1 | −1.69 |
| J | 2-(1,3-Thiazol-4-yl)ethanamine | MFCD08449088 | 7728-74-7 | NCCc1cscn1 | −1.696 |
| K | 1,3-thiazol-2-amine | MFCD00005325 | 96-50-4 | Nc1nccs1 | −1.323 |
| L | 2-(Aminomethyl)thiazole | MFCD02854204 | 55661-33-1 | NCc1nccs1 | −1.804 |
| M | (1,3-thiazolidin-4-yl)methanamine | CSC134590881 | | NCC1=CSCN1 | −1.591 |
| N | (Thiazol-4-yl)methanamine | MFCD06797207 | 16188-30-0 | NCc1cscn1 | −1.769 |
| O | (1,3-thiazol-4-yl)methanediamine | | | N[C@@H](c1cscn1)N | −1.76 |
| P | (1,3-thiazol-4-yl)methanolamine | | | N[C@@H](c1cscn1)O | −1.592 |
| Q | 4-(2-thienyl)-1,3-thiazol-2-amine | MFCD00457532 | 28989-50-6 | Nc1ncc(c2cccs2)s1 | −1.223 |
| R | [2-(thiophen-2-yl)-1,3-thiazol-4-yl]methanamine | MFCD02682000 | 321309-35-7 | NCc1csc(c2cccs2)n1 | −1.743 |
| S | [2-(thiophene-2-carbonyl)-1,3-thiazol-4-yl]methanamine | | 1525822-51-8 | NCc1csc(C(=O)c2cccs2)n1 | −1.943 |
| T | [2-(thiophen-2-ylmethyl)-1,3-thiazol-4-yl]methanamine | MFCD16779548 | 933756-07-1 | NCc1csc(Cc2cccs2)n1 | −2.264 |
| U | 1-[2-(4H-1,2,4-triazol-4-yl)-1,3-thiazol-4-yl]ethan-1-amine | MFCD20350672 | 1341722-22-2 | N[C@@H](c1csc(n1)n1cnnc1)C | −1.725 |
| V | {2-[4-(Trifluoromethyl)phenyl]-1,3-thiazol-4-yl}methylamine | MFCD06797507 | 769920-90-3 | NCc1csc(c2ccc(cc2)C(F)(F)F)n1 | −1.066 |

According to the binding energies provided in Table 1, molecules that appear to strongly bind to $Pb^{2+}$ ions are molecule 9 (4-(aminomethyl)-N-[3-(dimethylamino) methyl]-N-methyl-1,3-thiazol-2-amine), molecule 4 (4-(3-Aminopropyl)-1,3-thiazol-2-amine), molecule y ((2-{[4-(propan-2-yl)piperidin-1-yl]methyl}-1,3-thiazol-4-yl) methanamine), molecule v ({2-[(4-methylpiperidin-1-yl) methyl]-1,3-thiazol-4-yl}methanamine), molecule e ({2-[(3, 5-dimethylpiperidin-1-yl)methyl]-1,3-thiazol-4-yl}methanamine), molecule t (4-[(3-methyl-1-piperidinyl) methyl]-1,3-thiazol-2-amine), molecule d (4-[(3,5-dimethyl-1-piperidinyl)methyl]-1,3-thiazol-2-amine), and molecule 8 (4-(1-aminoethyl)-N-[2-(dimethylamino)ethyl]-N-methyl-1,3-thiazol-2-amine).

Apart from $Pb^{2+}$ ion binding energies, in order to explore the selectivity and sensitivity of each molecule toward $Pb^{2+}$ ion binding, the binding energies between each molecule and competitive ions, such as magnesium ions ($Mg^{2+}$), calcium ions ($Ca^{2+}$), sodium ions ($Na^+$), or protons ($H^+$), are also determined using the computing platform 20.

Figure 3A:
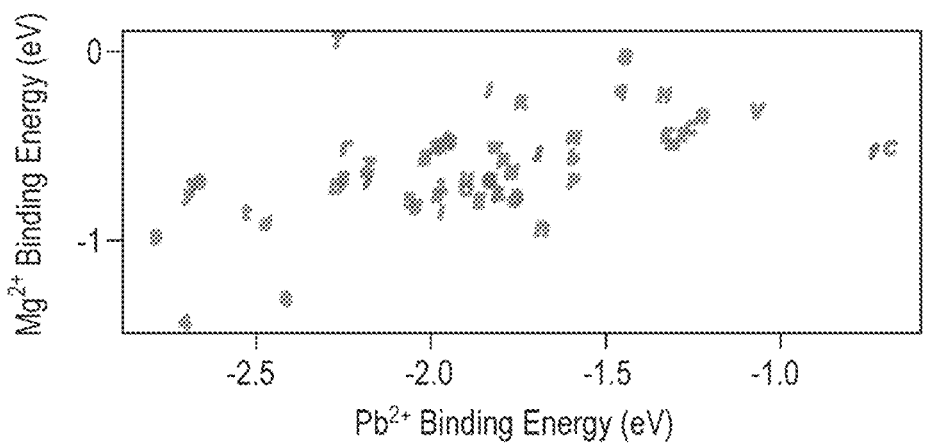
FIG. 3A depicts a schematic diagram of the binding energy between each molecule in Table 1 and a $Mg^{2+}$ ion versus the binding energy between each molecule in Table 1 and a $Pb^{2+}$ ion.

As generated by the computing platform 20, FIG. 3A depicts a schematic diagram of the binding energy between each molecule in Table 1 and a $Mg^{2+}$ ion vs. the binding energy between each molecule in Table 1 and a $Pb^{2+}$ ion. For a molecule to selectively bind to a $Pb^{2+}$ ion rather than a $Mg^{2+}$ ion, the molecule may exhibit a relatively more negative $Pb^{2+}$ ion binding energy and a relatively more positive $Mg^{2+}$ ion binding energy. Therefore, such a molecule may tend to locate in the upper left region of the diagram. As shown in FIG. 3A, molecules y, v, e, t, and d appear to exhibit relatively stronger $Pb^{2+}$ ion binding and weaker $Mg^{2+}$ ion binding.

Figure 3B:
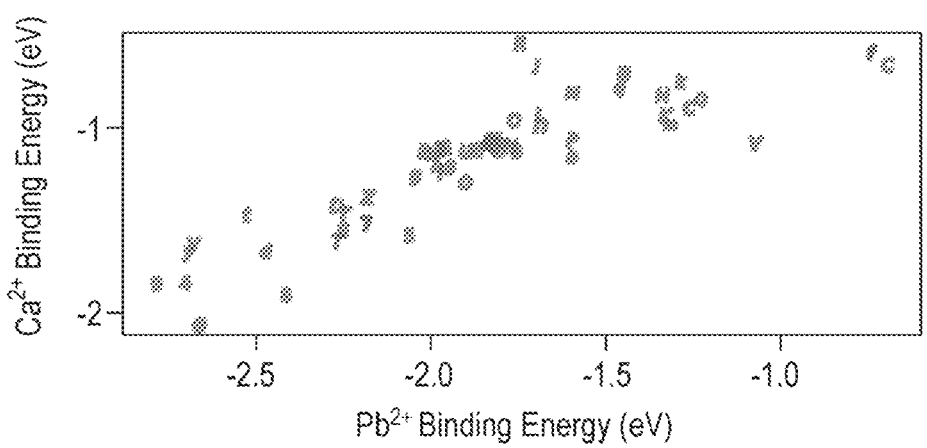
FIG. 3B depicts a schematic diagram of the binding energy between each molecule in Table 1 and a $Ca^{2+}$ ion versus the binding energy between each molecule in Table 1 and a $Pb^{2+}$ ion.

Similar results can be observed in FIG. 3B, which depicts a schematic diagram of the binding energy between each molecule in Table 1 and a $Ca^{2+}$ ion vs. the binding energy between each molecule in Table 1 and a $Pb^{2+}$ ion. Similarly, for a molecule to selectively bind to a $Pb^{2+}$ ion rather than a $Ca^{2+}$ ion, the molecule may exhibit a relatively more negative $Pb^{2+}$ ion binding energy and a relatively more positive $Ca^{2+}$ ion binding energy. Therefore, such a molecule may tend to locate in the upper left region of the diagram. As shown in FIG. 3B, molecules y, v, t, and d may show relatively stronger $Pb^{2+}$ ion binding and weaker $Ca^{2+}$ ion binding.

Figure 3C:
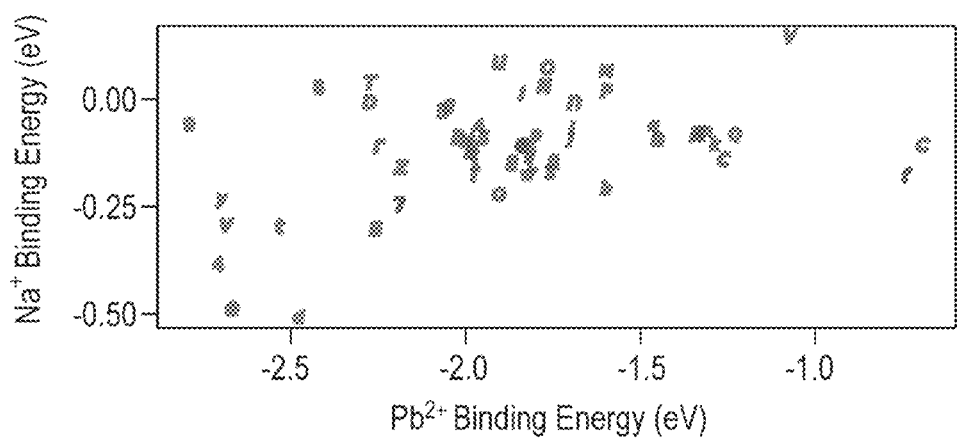
FIG. 3C depicts a schematic diagram of the binding energy between each molecule in Table 1 and a $Na^+$ ion versus the binding energy between each molecule in Table 1 and a $Pb^{2+}$ ion.

In addition, as generated by the computing platform 20, FIG. 3C depicts a schematic diagram of the binding energy between each molecule in Table 1 and a $Na^+$ ion vs. the binding energy between each molecule in Table 1 and a $Pb^{2+}$ ion. For a molecule to selectively bind to a $Pb^{2+}$ ion rather than a $Na^+$ ion, the molecule may exhibit a relatively more negative $Pb^{2+}$ ion binding energy and a relatively more positive $Na^+$ ion binding energy. Therefore, such a molecule may tend to locate in the upper left region of the diagram. As shown in FIG. 3C, molecules 9, y, v, t, and 4 may show relatively stronger $Pb^{2+}$ ion binding and weaker $Na^+$ ion binding.

Figure 3D:
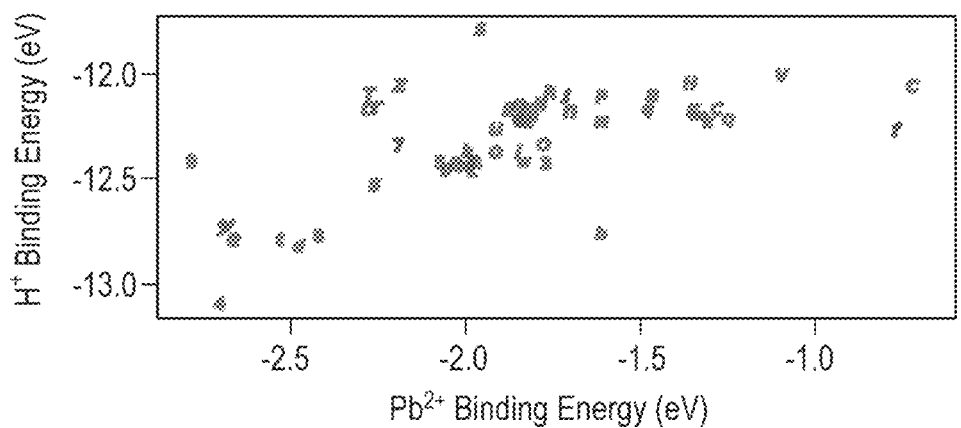
FIG. 3D depicts a schematic diagram of the binding energy between each molecule in Table 1 and a $H^+$ ion versus the binding energy between each molecule in Table 1 and a $Pb^{2+}$ ion.

Further, as generated by the computing platform 20, FIG. 3D depicts a schematic diagram of the binding energy between each molecule in Table 1 and a $H^+$ ion versus the binding energy between each molecule in Table 1 and a $Pb^{2+}$ ion. For a molecule to selectively bind to a $Pb^{2+}$ ion rather than $H^+$, the molecule may exhibit a relatively more negative $Pb^{2+}$ ion binding energy and a relatively more positive $H^+$ binding energy. Therefore, such a molecule may tend to locate in the upper left region of the diagram, where the molecules are less likely to be protonated. As shown in FIG. 3D, molecules 9, y, v, e, t, d, and 8 may show relatively stronger $Pb^{2+}$ ion binding and weaker $H^+$ binding.

Figure 3E:
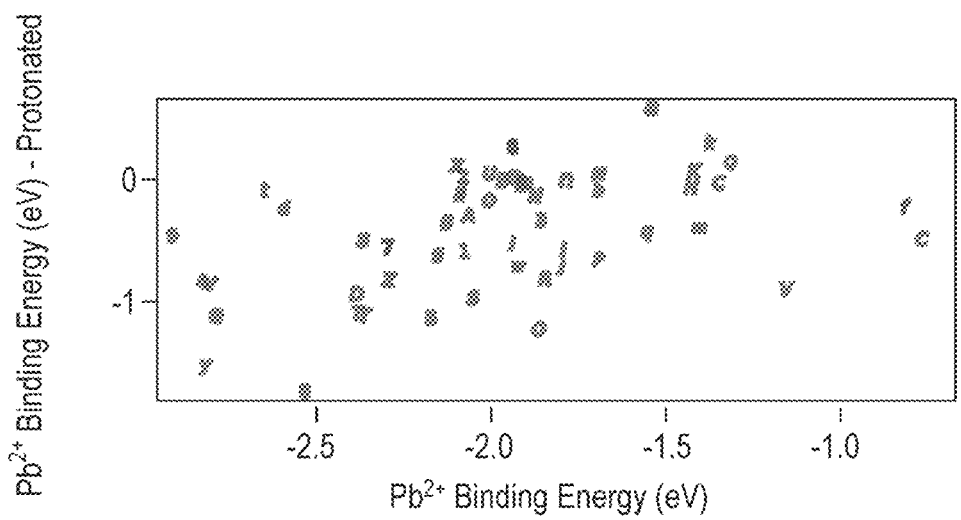
FIG. 3E depicts a schematic diagram of the binding energy between the protonated form of each molecule in Table 1 and a $Pb^{2+}$ ion versus the binding energy between each molecule in Table 1 and a $Pb^{2+}$ ion.

Moreover, as generated by the computing platform 20, FIG. 3E depicts a schematic diagram of the binding energy between the protonated form of each molecule in Table 1 and a $Pb^{2+}$ ion versus the binding energy between each molecule (i.e. not protonated form) in Table 1 and a $Pb^{2+}$ ion. In contrast to FIGS. 3A-3D, for a molecule to bind to a $Pb^{2+}$ ion with a higher sensitivity when the molecule is protonated (i.e. the binding is relatively pH insensitive), such a molecule may tend to locate in the lower left region of the diagram. As shown in FIG. 3D, molecules e, y, and 8 appear to exhibit relatively stronger $Pb^{2+}$ ion binding when each of the molecules is protonated.

Taken FIGS. 3A to 3E together, candidate molecules in each scenario are consistent with those identified in Table 1 (i.e. molecules 9, 4, y, v, e, t, d, and 8). However, although molecule 9 shows the relatively stronger $Pb^{2+}$ ion binding and better selectivity toward $Pb^{2+}$ ions in the presence of $Na^+$ and/or $H^+$ ions, molecule 9 is currently not commercially available. Further, although molecule 4 shows relatively stronger $Pb^{2+}$ ion binding against $Na^+$ ions, molecule 4 exhibits a relatively poor selectivity toward $Pb^{2+}$ ions in the presence of $Mg^{2+}$, $Ca^{2+}$, and/or $H^+$ ions. In addition, even though molecule e shows relatively stronger selectivity toward $Pb^{2+}$ ions in the presence of $Mg^{2+}$ and/or $H^+$ ions, molecule e exhibits relatively poor selectivity toward $Pb^{2+}$ ions when $Ca^{2+}$ and/or $Na^+$ ions are also present in a fluid medium. Moreover, molecule 8 appears to show a relatively poor selectivity toward $Pb^{2+}$ ions in the presence of $Mg^{2+}$, $Ca^{2+}$, and/or $Na^+$ ions.

On the other hand, molecules y, v, and d show relatively stronger $Pb^{2+}$ ion binding and better selectivity toward $Pb^{2+}$ ions, and each of them include a piperidine-based sidechain attached to the thiazole moiety of the thiazole-based receptor of each molecule. Additionally, molecule t not only shows relatively stronger $Pb^{2+}$ ion binding but also good selectivity toward $Pb^{2+}$ ions when $Mg^{2+}$, $Ca^{2+}$, $Na^+$, and/or $H^+$ ions are also present in a fluid medium.

In addition to the influence of the chemical structure of the thiazole-based receptor and the methylamine-based spacer, other factors may also influence the binding behavior (e.g. selectivity or sensitivity) of a chemosensor. Some of these factors may include the structure of a fluorophore bound to the methylamine-based spacer, the distance between the fluorophore and a binding ion, and the distance between an electronegative atom (e.g. N, O, or S) of the thiazole-based receptor and a binding ion. For instance, among the molecules discussed above, results also indicate that molecules 4, e, and t are more likely to show weak fluorescence due to the proximity of the fluorophore of each molecule to the $Pb^{2+}$ ion. Furthermore, economic reasons (e.g. cost or feasibility of synthesizing a chemosensor) may also need to be considered in the selection of a chemosensor for a selective ion sensing.

Moreover, results in Table 1 and FIGS. 3A to 3E also indicate that introducing sidechains to either the thiazole-based receptor or the methylamine-based spacer of a chemosensor may enhance the selectivity of the chemosensor toward $Pb^{2+}$ ion binding. Further, due to the high reactivity of halogens, such as fluorine (F) or chlorine (Cl), adding halogens to either the thiazole-based receptor or the methylamine-based spacer of a chemosensor may be adverse to the $Pb^{2+}$ ion binding.

Figure 4:
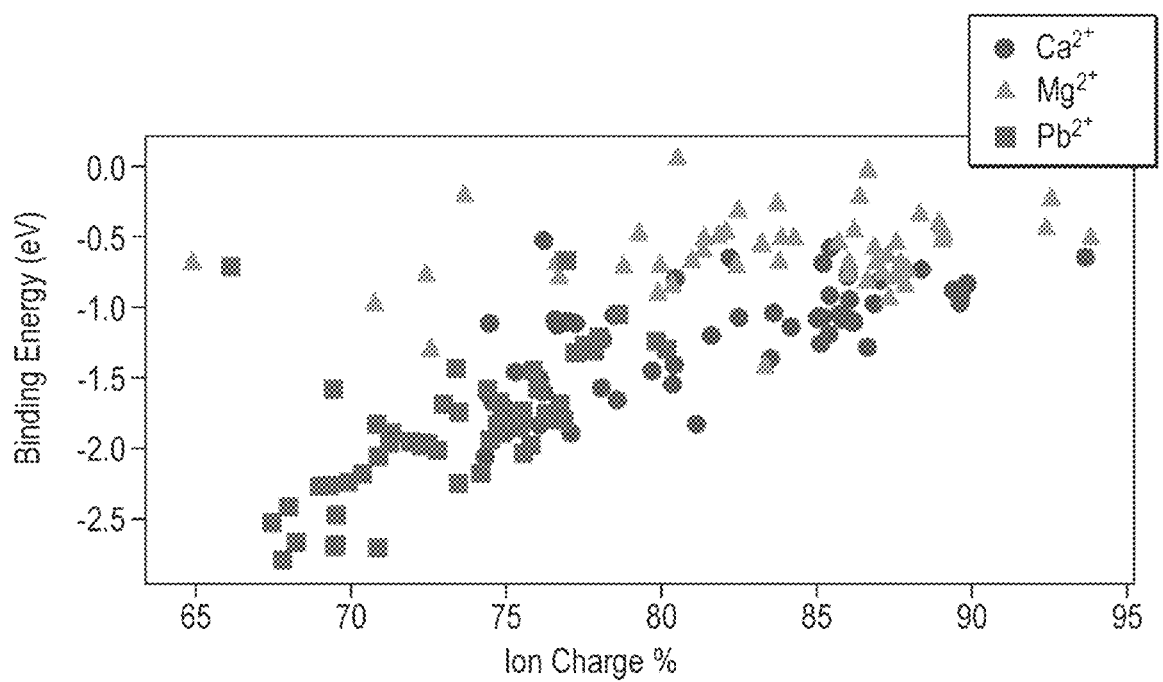
FIG. 4 depicts a schematic diagram of the binding energy (eV) between each molecule in Table 1 and an ion versus the amount of ion charge (%) of the ion.

FIG. 4 depicts a schematic diagram of the binding energy (eV) between each molecule in Table 1 and an ion versus the amount of ion charge (%) of the ion. The ion may be $Ca^{2+}$ (circle), $Mg^{2+}$ (triangle), or $Pb^{2+}$ (square), respectively. As shown in FIG. 4, the binding energy between each molecule and an ion is roughly linear to the amount of ion charge (%) of the corresponding ion. For example, a stronger $Pb^{2+}$ binding energy appears to correspond to a smaller amount of ion charge (%) on Pb (i.e. the charge on Pb is less than 2+). In addition, as the amount of ion charge (%) on Pb increases, the $Pb^{2+}$ binding strength appears to be decreasing. Similar results can be observed in $Ca^{2+}$ and $Mg^{2+}$ binding scenarios. These results indicate that the ion binding process may not only be a Coulomb interaction, but also influenced by the propensity of charge transfer. Such a charge transfer process may occur from a neighboring atom (i.e. an electron-donating atom positioned relatively close to the binding ion) to the binding ion. Therefore, depending on the chemical structure of the thiazole-based receptor, the methylamine-based spacer, and/or the fluorophore, and depending on the distance between each of the thiazole-based receptor, the methylamine-based spacer, and/or the fluorophore to the binding ion, a high propensity of charge transfer may increase an electron density at or near the binding site, thereby contributing to a relatively stronger ion binding.

Figure 5A:
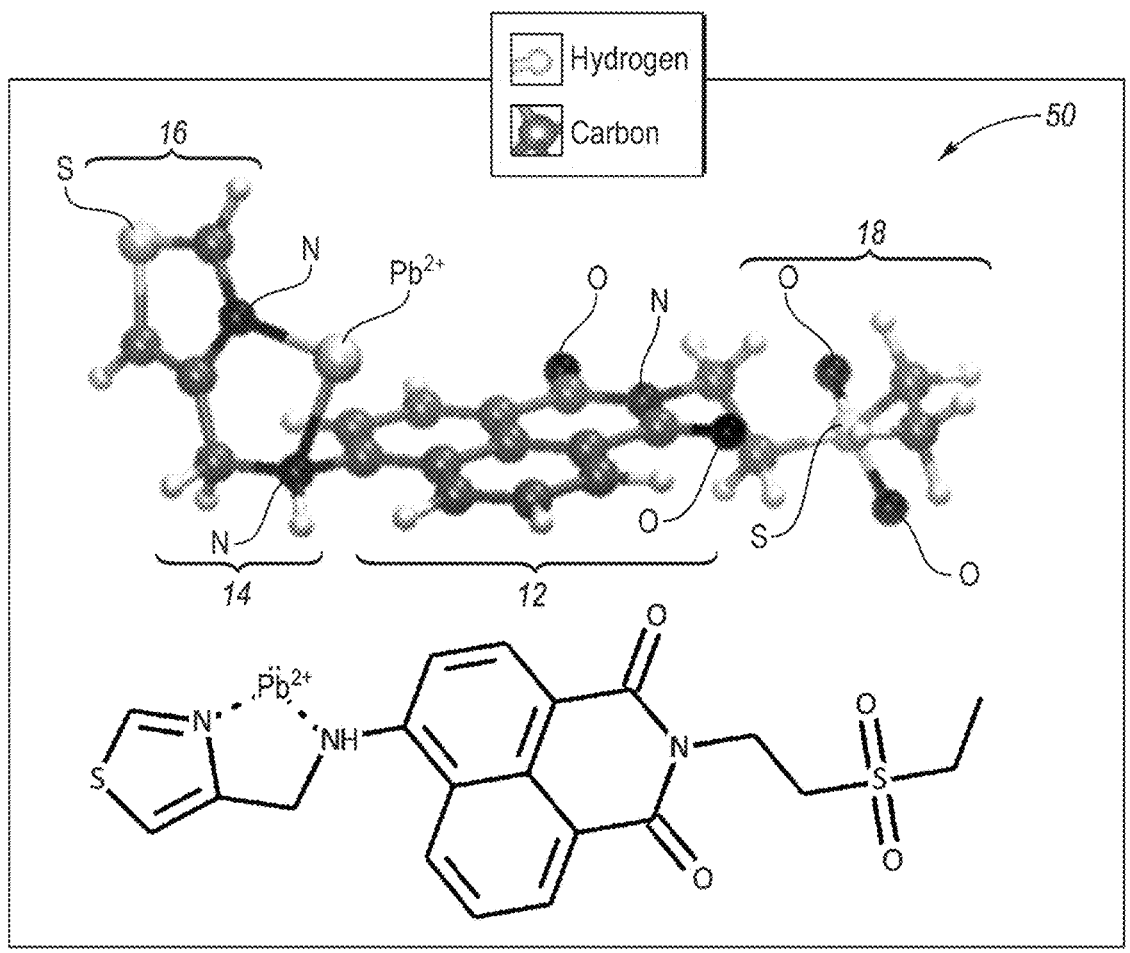
FIG. 5A depicts a schematic diagram of an exemplary chemosensor according to the present disclosure.

FIG. 5A depicts a schematic diagram of an exemplary chemosensor according to the present disclosure. As shown in FIG. 5A, the chemosensor 50 includes a thiazole receptor, a methylamine spacer, and a 1,8-naphthalimide fluorophore. The chemosensor may coordinate to a $Pb^{2+}$ ion via the N atom of the thiazole receptor and the N atom of the methylamine spacer. In addition, the fluorophore may be attached to an anchor, which is diethyl sulfone.

Figure 5B:
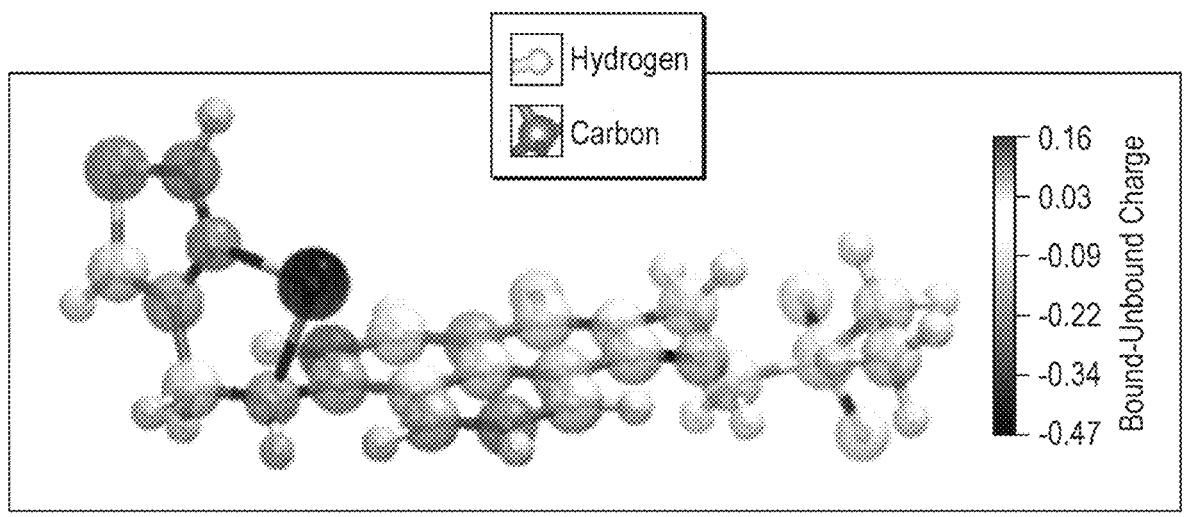
FIG. 5B depicts a schematic diagram illustrating the effect of charge transfer in the chemosensor described in FIG. 5A upon a $Pb^{2+}$ ion binding.

FIG. 5B depicts a schematic diagram illustrating the effect of charge transfer in the chemosensor described in FIG. 5A upon a $Pb^{2+}$ ion binding. As shown in FIG. 5B, atoms of the chemosensor may either lose or gain charges upon the $Pb^{2+}$ ion binding. The charge difference between a bound state (i.e. when the chemosensor binds to a $Pb^{2+}$ ion) and an unbound state (i.e. when the chemosensor does not bind to a $Pb^{2+}$ ion) may represent the amount of charge transfer from each atom to the $Pb^{2+}$ ion. Specifically, a negative charge difference indicates a loss of charges (i.e. gain electrons) upon the $Pb^{2+}$ ion binding. On the contrary, a positive charge difference indicates a gain of charges (i.e. lose electrons) upon the $Pb^{2+}$ ion binding.

Referring to FIG. 5B, the $Pb^{2+}$ ion exhibits a negative charge difference, which, accordingly, indicates that upon the $Pb^{2+}$ ion binding, the $Pb^{2+}$ ion loses charges (i.e. the charge on Pb is less than 2+). This also shows that upon the $Pb^{2+}$ ion binding, at least one neighboring atom transfers electrons to the $Pb^{2+}$ ion, thereby facilitating the $Pb^{2+}$ ion binding. Similarly, the N atom of the thiazole receptor and the N atom of the methylamine spacer both exhibit negative charge differences, which indicate that both N atoms lose charges (i.e. gain electrons) upon the $Pb^{2+}$ ion binding. On the other hand, the S atom of the thiazole receptor exhibits a positive charge difference, which means that upon the $Pb^{2+}$ ion binding, the S atom loses electrons. Similarly, the positive charge differences of the atoms in the fluorophore also indicate that these atoms donate electrons to facilitate the $Pb^{2+}$ ion binding.

Figures 6, 7:
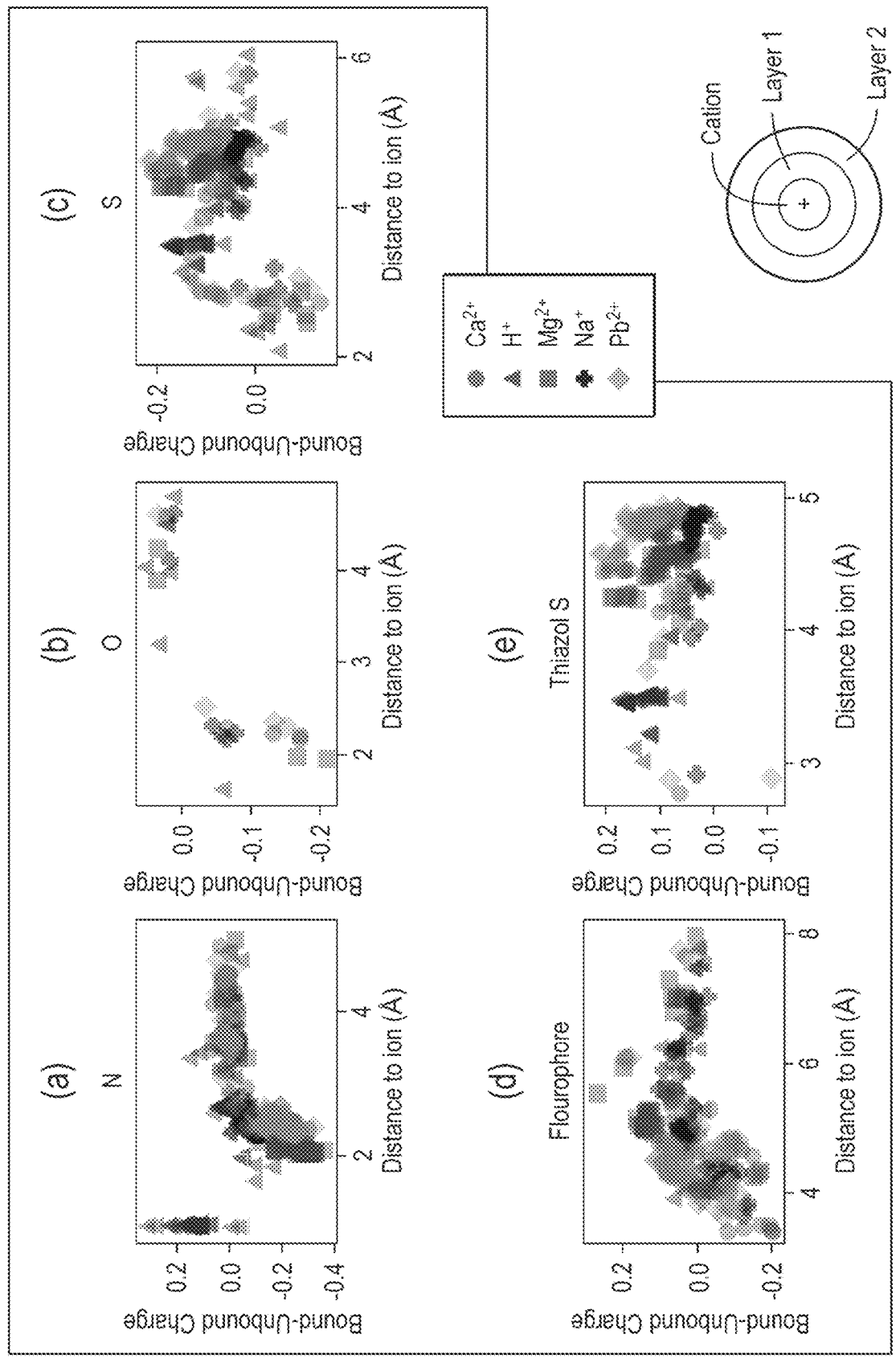
FIG. 6 depicts schematic diagrams of the amount of charge transfer upon each molecule in Table 1 binding to an ion versus the distance between a moiety of a chemosensor to the ion.
FIG. 7 depicts a schematic diagram illustrating a double-layer electrostatics effect as described in FIG. 6.

FIG. 6 depicts schematic diagrams of the amount of charge transfer upon each molecule in Table 1 binding to an ion vs. the distance between a moiety of a chemosensor to the ion. The ion may be $Ca^{2+}$ (circle), $H^+$ (triangle), $Mg^{2+}$ (square), $Na^+$ (cross), or $Pb^{2+}$ (rhombus), respectively. The moiety of the chemosensor may be (a) the N atom of the thiazole moiety of the thiazole-based receptor; (b) an O atom, if any, of the thiazole-based receptor; (c) a S atom, if any, of the thiazole-based receptor; (d) a 1,8-naphthalimide fluorophore; and (e) the S atom of the thiazole moiety of the thiazole-based receptor, respectively.

Referring to FIG. 6, the amount of charge transfer from each of the moiety to the binding ion may vary depending on the distance between the moiety to the binding ion. Specifically, in FIGS. 6(a) through (c), upon an ion binding, each neighboring atom shows negative charge differences when the distance between each moiety and a binding ion is between 2 and 3 Å (or between 2 and 3.5 Å for FIG. 6(a)). These results indicate that upon the ion binding, the neighboring atom loses charges (i.e. gain electrons). On the other hand, in FIG. 6(d), upon an ion binding, the charge differences are mostly positive when the distance between the fluorophore and a binding ion is farther than 3.5 Å. These results indicate that upon the ion binding, the fluorophore donates electrons to the neighboring atoms and the binding ion, thereby causing the fluorophore to gain charges. Similarly, in FIG. 6(e), upon an ion binding, the charge differences of the S atom of the thiazole moiety of the thiazole-based receptor are mostly positive when the distance between the S atom and a binding ion is farther than 3.5 Å. This also indicates that upon the ion binding, the S atom donates electrons to the neighboring atoms and the binding ion, thereby gaining charges.

FIG. 7 depicts a schematic diagram illustrating a double-layer electrostatics effect as described in FIG. 6. As discussed in FIG. 6, upon an ion binding, the neighboring atoms, such as N, O, and S, may gain electrons (i.e. lose charges) when the distance between each neighboring atom and a binding ion is generally between 2 and 3.5 Å. Such an effect may form a "negative shell" (Layer 1) around the binding ion. In addition, because the fluorophore and the S atom of the thiazole moiety of the thiazole-based receptor, upon the ion binding, donate electrons to the neighboring atoms and the binding ion when the distance between either of the fluorophore or the S atom and the binding ion is generally farther than 3.5 Å, the fluorophore and the S atom thus gain charges, thereby forming a "positive shell" (Layer 2) around Layer 1. Therefore, the propensity of charge transfer from the fluorophore and the S atom of the thiazole moiety of the thiazole-based receptor may create a double-layer electrostatics effect around the binding ion. Such an effect may help to screen and identify chemosensors that can strongly and selectively bind to $Pb^{2+}$ ions.

Based on the results illustrated in FIGS. 3A-3E and the double-layer electrostatics effect described in FIG. 7, FIG. 8 depicts candidates of chemosensors configured for selective $Pb^{2+}$ ion sensing. As shown in FIG. 8, each chemosensor in FIG. 8 includes a thiazole-based receptor, a methylamine-based spacer bound to the thiazole-based receptor, a 1,8-naphthalimide fluorophore bound to the methylamine-based spacer, and an anchor bound to the fluorophore. The anchor is diethyl sulfone.

Figures 8A, 8B:
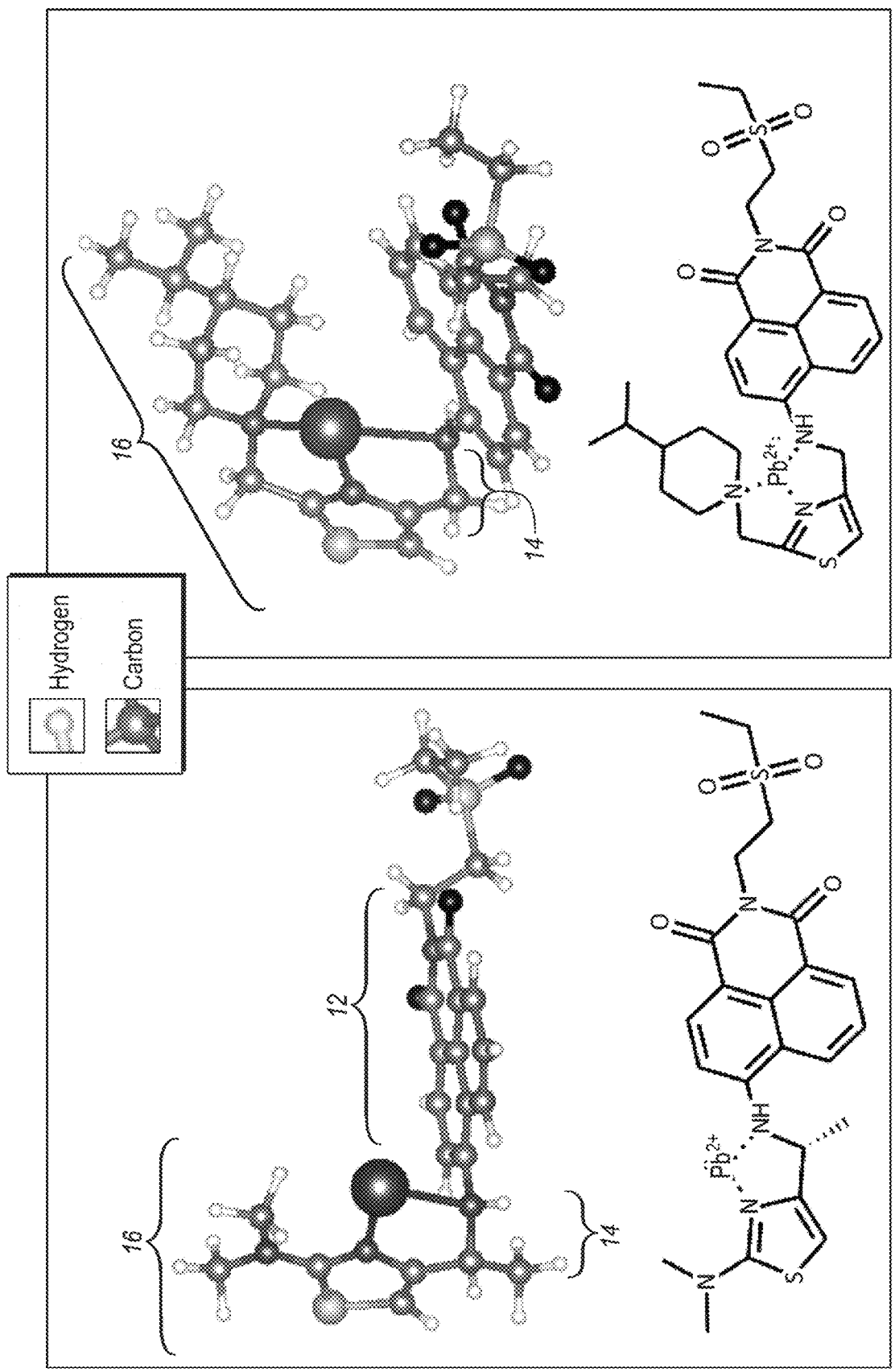
FIGS. 8A-E depicts candidates of chemosensors configured for selective $Pb^{2+}$ ion sensing.
Figure 8D:
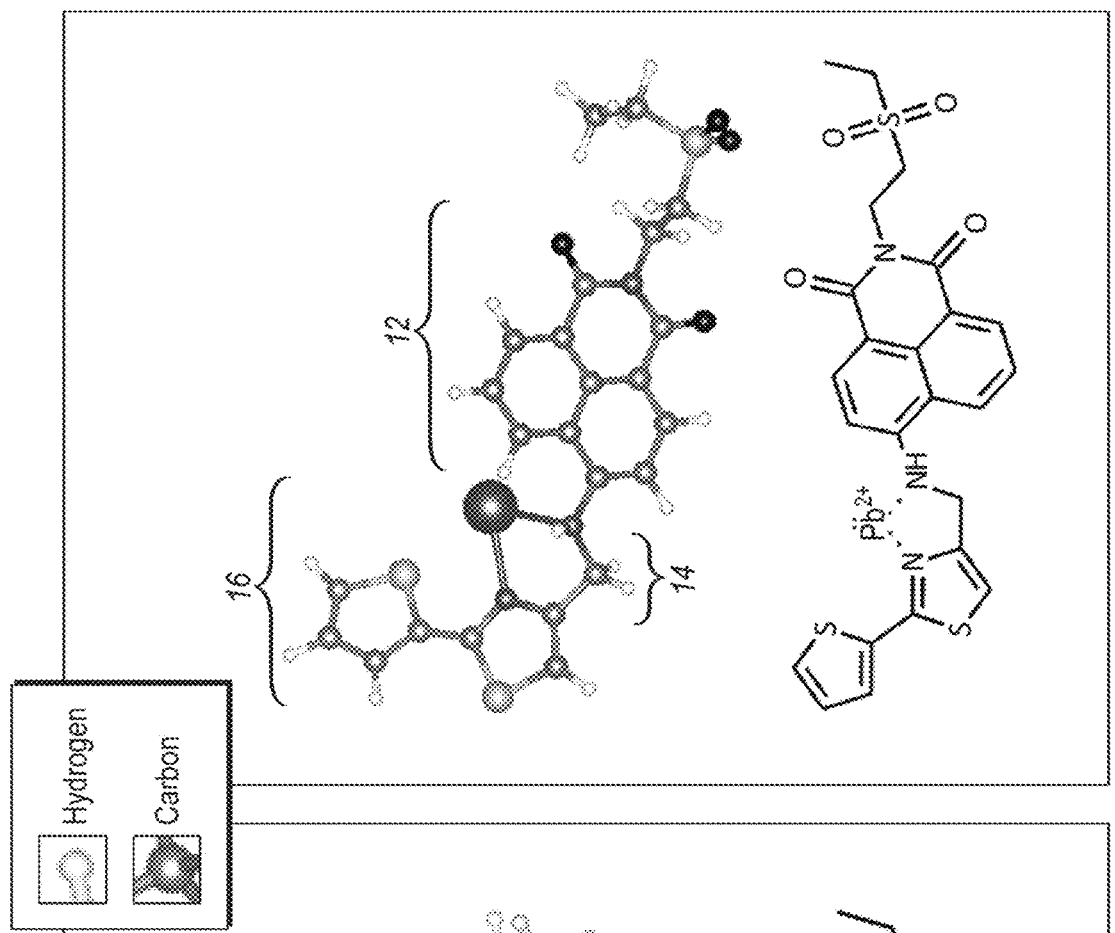
Figure 8C:
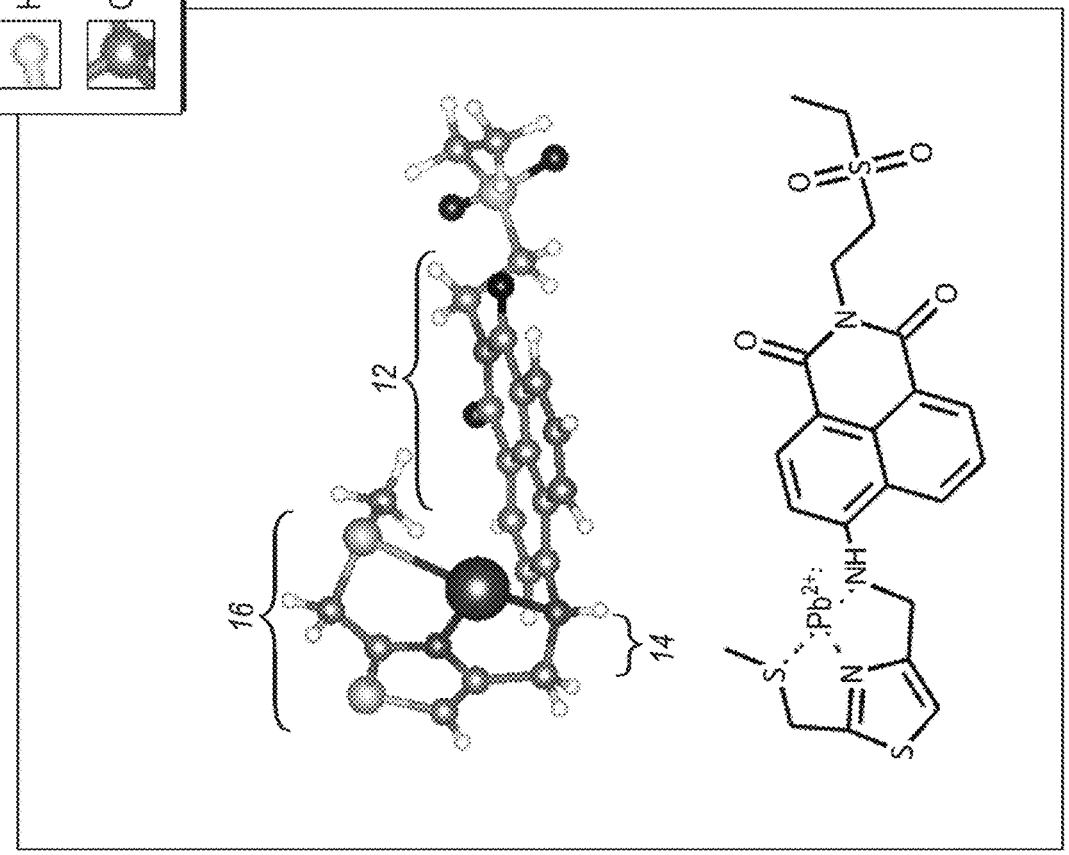
Figure 8E:
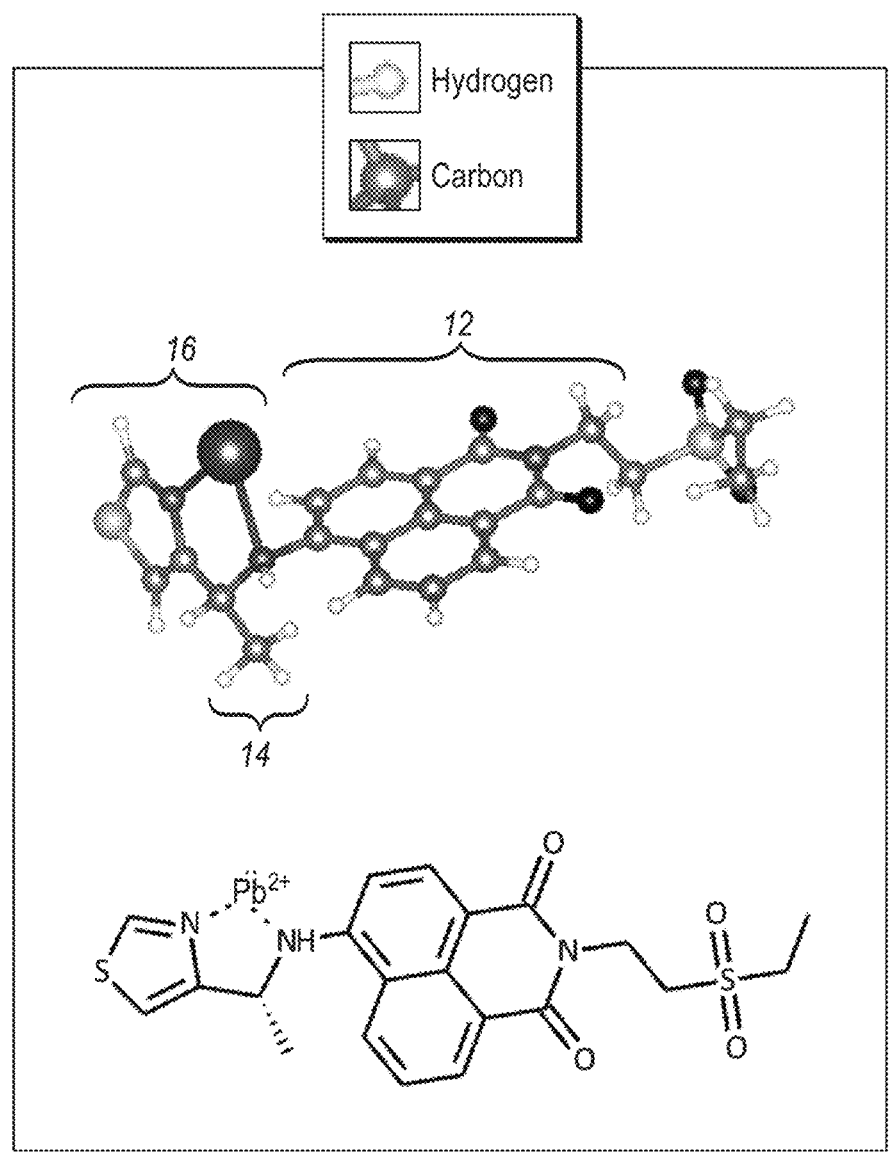

Specifically, FIGS. 8(a) and 8(e) depict chemosensors that include a methyl group sidechain attached to the methylamine-based spacer. FIG. 8(b) depicts a chemosensor that includes a piperidine-based sidechain attached to the thiazole moiety of the thiazole-based receptor. In addition, FIGS. 8(c) and 8(d) depict chemosensors that include a sulfur-containing group attached to the thiazole moiety of the thiazole-based receptor. Particularly, the sulfur-containing group in FIG. 8(c) is a sulfide group, and the sulfur-containing group sidechain in FIG. 8(d) is a thiophenyl group.

Figure 9:
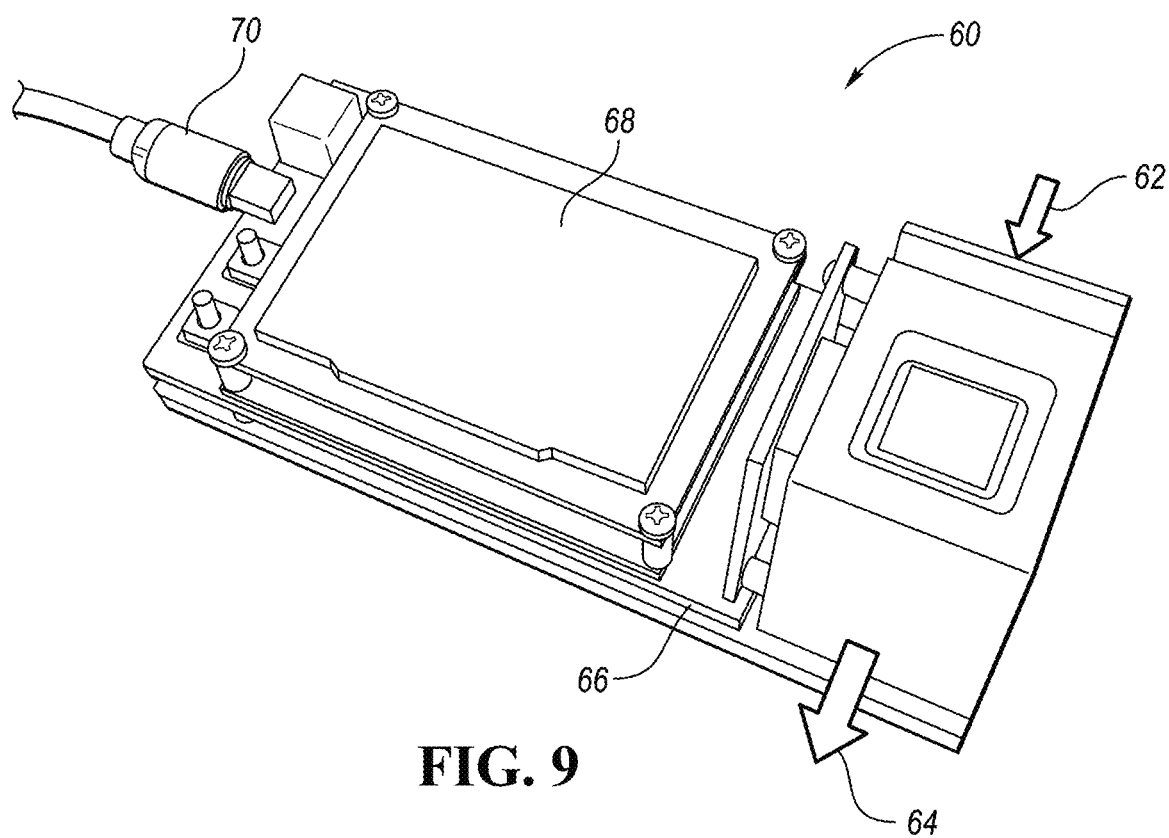
FIG. 9 depicts a schematic and perspective view of a sensing device configured to detect ions in a fluid medium.

FIG. 9 depicts a schematic and perspective view of a sensing device configured to detect ions, especially $Pb^{2+}$ ions, in a fluid medium (e.g. water). As shown in FIG. 9, the sensing device 60 includes an inlet 62, an outlet 64, a sensor (not shown) configured to detect ions in the fluid medium, and a detector 66. The detector 66 may be a photodetector. The sensor may be a chemosensor as described above. In one embodiment, the chemosensor is a receptor-spacer-fluorophore type of sensor, where the spacer is methylamine, and the receptor includes an unsaturated heterocycle ring bound to the spacer and further includes at least one sidechain bound to the unsaturated heterocycle ring. In another embodiment, the chemosensor is a receptor-spacer-fluorophore type of sensor, where the spacer is methylamine with at least one sidechain, and the receptor includes an unsaturated heterocycle ring bound to the spacer.

Referring to FIG. 9, after the fluid medium enters the sensing device 60 via the inlet 62, the sensor may capture $Pb^{2+}$ ions in the fluid medium, thereby generating a signal (e.g. fluorescence). The detector 66 may collect the signal, and based on the signal, calculate a concentration of the $Pb^{2+}$ ions in the fluid medium. The sensing device 60 may further include an electronic screen 68, which may display information related to an ion sensing event, such as the concentration of the $Pb^{2+}$ ions in the fluid medium. In some embodiments, the sensing device 60 may transmit the information to a remote location configured to record and store the information. For example, the information may be transmitted wirelessly or through a cable 70 connected to the sensing device 60.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the present disclosure that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A compound comprising:
   a 1,8-naphthalimide fluorophore;
   a spacer bound to the 1,8-naphthalimide fluorophore, the spacer being —$CH_2$—NH—; and
   a thiazole-based receptor bound to the spacer.

2. The compound of claim 1, wherein the thiazole-based receptor includes at least two electronegative atoms.

3. The compound of claim 1, wherein the compound includes electronegative atoms facilitating a capture of $Pb^{2+}$ ion from a fluid.

4. The compound of claim 1, further comprising a sulfur-based anchor bound to the 1,8-naphthalimide fluorophore.

5. The compound of claim 1, wherein the thiazole-based receptor has a moiety sidechain that is a piperidinyl group or a sulfur-containing group.

6. A compound comprising:
   a 1,8-naphthalimide fluorophore;
   a spacer bound to the 1,8-naphthalimide fluorophore, the spacer being —CH(R)—NH—, wherein R is $CH_3$; and
   a thiazole-based receptor bound to the spacer, the thiazole-based receptor having a moiety sidechain that is dimethylamine.

7. A chemosensor configured to capture an ion in a fluid medium, the chemosensor comprising:
   a 1,8-naphthalimide fluorophore;
   a spacer bound to the 1,8-naphthalimide fluorophore, the spacer being —$CH_2$—NH—; and
   a thiazole-based receptor bound to the spacer,
   the chemosensor including at least two electronegative atoms facilitating capture of the ion from fluid medium.

8. The chemosensor of claim 7, wherein the ion is $Pb^{2+}$ ion.

9. The chemosensor of claim 7, further comprising a sulfur-based anchor bound to the 1,8-naphthalimide fluorophore.

10. The chemosensor of claim 7, wherein the thiazole-based receptor has a moiety sidechain that is a piperidinyl group or a sulfur-containing group.

11. A sensing device comprising:
    a chemosensor configured to capture an ion in a fluid medium and to generate a signal in response to capturing the ion, the chemosensor including:
    a 1,8-naphthalimide fluorophore;
    a spacer bound to the 1,8-naphthalimide fluorophore, the spacer being —$CH_2$—NH—; and
    a thiazole-based receptor bound to the spacer, the spacer and the thiazole-based receptor configured to capture the ion to generate the signal.

12. The sensing device of claim 11, wherein the thiazole-based receptor includes at least two electronegative atoms.

13. The sensing device of claim 11, further comprising a sulfur-based anchor bound to the 1,8-naphthalimide fluorophore and configured to link the chemosensor to cellulose microparticles.

14. The sensing device of claim 13, wherein the cellulose microparticles are embedded in a hydrogel.

15. The sensing device of claim 11, wherein the ion is $Pb^{2+}$ ion.

16. The sensing device of claim 11, wherein the thiazole-based receptor has a moiety sidechain that is a piperidinyl group or a sulfur-containing group.

* * * * *